United States Patent [19]

Scolastico

[11] Patent Number: 4,788,212

[45] Date of Patent: Nov. 29, 1988

[54] PYRROLIDIN-2-ONE DERIVATIVES HAVING NOOTROPIC ACTIVITY

[75] Inventor: Silvia Scolastico, Milan, Italy

[73] Assignees: Gibipharma S.p.A.; Istituto Biochimico Italiano Giovanni Lorenzini S.p.A., both of Milan, Italy; a part interest

[21] Appl. No.: 79,172

[22] Filed: Jul. 29, 1987

[30] Foreign Application Priority Data

Aug. 1, 1986 [IT] Italy .................... 21397 A/86

[51] Int. Cl.$^4$ ............... A61K 31/40; C07D 207/12
[52] U.S. Cl. ........................ 514/422; 548/523
[58] Field of Search ..................... 548/523; 514/422

[56] References Cited

PUBLICATIONS

The Merck Index, 10th Ed., (1983), p. 1080.

Butler, et al., Journal of Medicinal Chemistry, (1984), vol. 27, pp. 684–691.

*Primary Examiner*—Joseph Paul Brust
*Attorney, Agent, or Firm*—Walter H. Schneider

[57] ABSTRACT

Pyrrolidin-2-one derivatives of formula I:

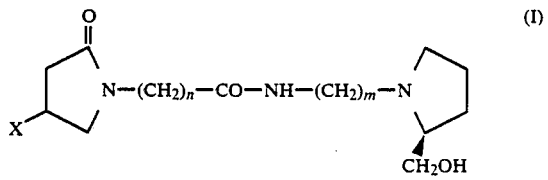

wherein X=H, OH, $C_2$-$C_7$ acyloxy, $C_1$-$C_6$ alkoxy, cycloalkoxy or phenoxy, n=0 or 1 and m=2 or 3, have a marked nootropic activity.

5 Claims, No Drawings

PYRROLIDIN-2-ONE DERIVATIVES HAVING NOOTROPIC ACTIVITY

The present invention refers to pharmacologically active pyrrolidinone derivatives, to synthetic method therefor and to pharmaceutical compositions containing them.

More particularly, the invention refers to compounds having the following general formula:

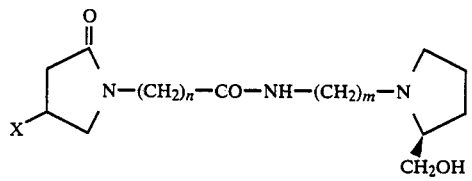

wherein X is hydrogen or an OR group, wherein R has one of the following meanings: hydrogen, $C_2$-$C_7$ acyl, saturated or unsaturated $C_1$-$C_6$ alkyl, cycloalkyl, aralkyl or phenyl, n represents zero or 1 and m represents 2 or 3.

According to the invention, the compounds I are obtained by aminolysis of compounds of formula II with L-prolinol-aminoalkyl derivatives III, according to the scheme A:

Scheme A

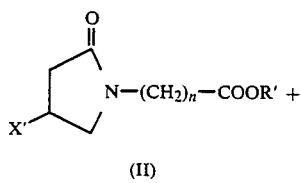

wherein X' has the meanings already stated for X, except those of acyloxy residue, and may moreover represent a $CH_3OCH_2O-$ or $CH_3OCH_2CH_2O-$ residue; R' is a lower alkyl residue, preferably methyl or ethyl; n and m are as above defined.

The formation of the amide bond described in the scheme A may be carried out also by activating the carboxy group of compounds IV, by reaction with N,N'-carbonyldiimidazole (NCDI) or with 2-ethoxy-1-ethoxycarbonyl-1,2-dihydroquinoline (EEDQ), and subsequent condensation with (III) (scheme B):

Scheme B

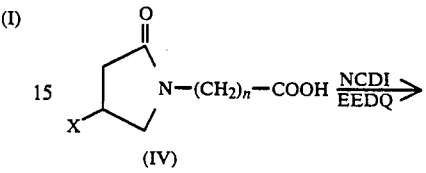

wherein Y represents

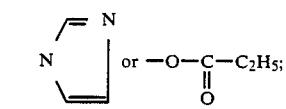

whereas X, n and m are as above defined.

The acids IV or the esters II, wherein X is H, OH, alkoxy or acyloxy are known compounds (for X=H cfr D. E. Butler and coll. J. Med. Chem., 27, 684 (1984); for X=OH and X=OCOCH$_3$ cfr G. Pifferi and M. Pinza, U.S. Pat. No. 4,118,396).

The synthesis of L-prolinol-N-aminoalkyl derivatives III is carried out according to the scheme C (m=2) or D (m=3):

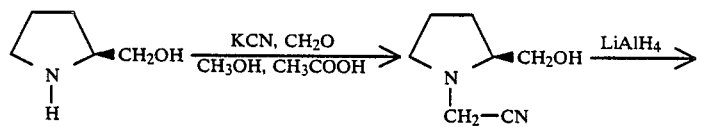

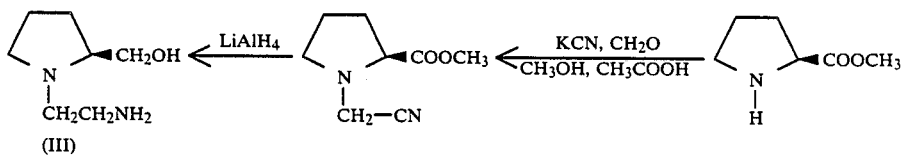

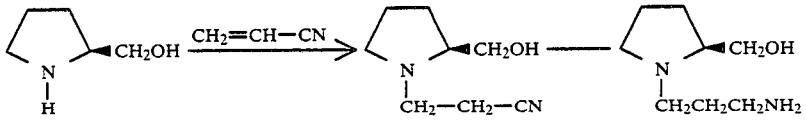

The compounds of the invention show a very interesting activity on the Central Nervous System: they have been tested in comparison to controls and to a known compound having similar structure and pharmacological behaviour, i.e. Piracetam or 2-(pyrrolidin-2-one)acetamide. The compounds have been tested, for the memory and learning, in the following way:

Active avoidance behaviour test

The experimental method was substantially that described by Fuxe and Hanson "Central catecholamine neurons and conditioned avoidance behaviour" (Psychopharmacologie, 11, 439–447, 1967), i.e. the "Shuttle box" method.

A perspex cage 60×30×20 cm, divided in two compartments by a diaphragm, has been used.

The bottom of the cage is provided by an electrifiable adjustable grid. A luminous and sonorous signal is provided in each compartment.

In the learning test, each rat is subjected to a cycle of 20 attempts during which the animal must learn to avoid the electrical schock changing compartment within 6 seconds from the luminous and sonorous signal.

The distance from an attempt to the following one is 30 seconds (+20% at random).

Whenever the animal does not avoid the schock, the latter is anyhow interrupted after 3 seconds.

The apparatus records the latency times to the response; the maximum time corresponds to 6 warning seconds plus 3 seconds of stimulus.

Both substances have been administered i.p. in saline solution at a dose of 200 mg/kg 30' after each experimental session.

Piracetam, in the used experimental conditions, improves learning, significantly reducing the latency time.

The compound GB 116 I (X=H; n=1, m=2), possesses higher activity than Piracetam on the latency time (table 1).

TABLE 1

Effect of GB 116 (I; X = H) on the active avoidance.
Latency time in apparatus units (mean ± D.S.)

| DAY | CONTROLS | PIRACETAM | GB 116 (I; X = H) |
|---|---|---|---|
| 1 | 110 + 30 | 104 + 13 | 147 + 21 |
| 2 | 108 + 29 | 98 + 31 | 106 + 29 |
| 3 | 103 + 35 | 85 + 23 | 85 + 24 |
| 4 | 98 + 39 | 85 + 30 | 84 + 27 |
| 5 | 103 + 44 | 90 + 44 | 84 + 40 |
| 6 | 100 + 41 | 91 + 43 | 88 + 44 |
| 7 | 96 + 42 | 86 + 40 | 85 + 32 |
| 8 | 103 + 36 | 87 + 34 | 80 + 33 |
| 9 | 102 + 45 | 88 + 30 | 76 + 30 |

The following examples further illustrate the invention without limiting it.

EXAMPLE 1

(a) [N-cyanomethyl(S)-2-hydroxymethyl)]pyrrolidine

Formaldehyde (0.358 ml of 40% aqueous solution) and KCN (258 mg) were added to a solution of (S)(+)-2-hydroxymethylpyrrolidine (400 mg) in methanol (2.3 ml). The mixture was warmed to 60° C. and acetic acid was added thereto (0.340 ml).

After 20' the solvent was evaporated, the residue was dissolved in the minimum amount of water and extracted with chloroform. The organic phase was washed with a saturated NaHCO₃ aqueous solution, dried on Na₂SO₄, filtered and evaporated.

The residue was distilled at 30 mm Hg; b.p. 170°–172° C. $[\alpha]_D^{20} = -45°$ (C=1,01, CHCl₃).

I.R. 3490, 2960, 2875, 2225, 1600 cm$^{-1}$ (CHCl₃) for $C_7H_{12}N_2O$: calc. % C 59.97, H 8.63, N 19.98. found % C 59.81, H 8.75, N 19.77.

(b) [N-(2-aminoethyl)(S)-2-(hydroxymethyl)]pyrrolidine

The compound obtained in (a) (1 g) in tetrahydrofuran (5 ml) was added at room temperature to a stirred suspension of LiAlH₄ (1.085 mg) in tetrahydrofuran (30 ml). After 15 hours reflux, H₂O (0.51 ml) and 10% NaOH (1.82 ml) were added. The organic phase was separated, dried on Na₂SO₄ and evaporated.

The residue was distilled at 25 mm Hg; b.p. 160° C. $[\alpha]_D^{20} = -23.5°$ (C=1.05 CHCl₃).

I.R. (CHCl₃) 3300, 2950, 2870, 2800 cm$^{-1}$ for $C_7H_{16}N_2O$: calc. % C 58.29, H 11.18, N 19.42. found % C 58.01, H 11.38, N 19.30.

(c) [N-[2-aminoethyl](S)-2-(hydroxymethyl)pyrrolidine]-2-keto-1-pyrrolidinacetamide (formula I; X=H; n=1; m=2)

The mixture of ethyl 2-keto-1-pyrrolidine acetate (1.2 g) and of the product of (b) (5.8 g) is warmed in oil-bath to 100°. After 2 hours the unreacted ester and amine were evaporated and the residue was purified by flash chromatography with the CHCl₃/CH₃OH/ET₃N 95/5/2 system, obtaining the title product in a 60% yield, as a pure oil.

$[\alpha]_D^{20} = -28.1$ (c=0.96% in CHCl₃).

I.R. (CHCl₃) 3400, 2995, 2960, 2865, 2810, 1675 cm$^{-1}$ for $C_{13}H_{23}N_3O_3$: calc. % C 57.96, H 8.60, N 15.60. found % C 57.86, H 8.81, N 15.55.

EXAMPLE 2

(a) N-cyanomethyl(S)-proline, methylester

KCN (390 mg) in H₂O (1 ml) and CH₂O (0.78 mol. of a 40% aqueous solution) were added to the aqueous solution of proline hydrochloride methylester (1 g in 5 ml). After 17 hours at room temperature the aqueous phase was extracted more times with CHCl₃. The mixture was washed with saturated NaHSO₃ aqueous solution and then with H₂O. The organic phase was dried on Na₂SO₄ and evaporated. The residue was filtered on silica, eluting with CHCl₃/MeOH 95:5. After distillation $[\alpha]_D^{20} = -125°$ (C=0.995 in CHCl₃).

I.R. (CHCl₃) 2990, 2960, 2835, 2220, 1745, 1440 cm$^{-1}$ for $C_8H_{12}N_2O_2$: calc. % C 57.12, H 7.19, N 16.65. found % C 57.22, H 7.30, N 16.85.

(b)
[N-(2-Aminoethyl)(S)-2-hydroxymethyl)]pyrrolidine

The compound (a) (1 g) was added to a stirred suspension of LiAlH$_4$ (1.81 g) in tetrahydrofuran (60 ml). The mixture was refluxed and after 1.5 h H$_2$O and 10% NaOH, respectively 1.64 ml and 3.25 ml were added. The mixture was stirred till the residue became white. After filtration and drying on Na$_2$SO$_4$, the solvent was evaporated and the product distilled. Almost quantitative yield.

(c)
[N-[2-Aminoethyl](S)-2-(hydroxymethyl)pyrrolidine]-2-keto-1-pyrrolidinoacetamide (formula I, with X=H; n=1; m=2)

The same procedure of example 1 was followed.

EXAMPLE 3
[N-[2-Aminoethyl](S)-2-(hydroxymethyl)pyrrolidine]-2-keto-1-pyrrolidinoacetamide (formula I; with X=H; n=1; m=2)

N,N'-carbonylidiimidazole (6.09 g) was added under N$_2$ atmosphere to a suspension of 2-keto-1-pyrrolidin acetic acid (3 g) in CH$_2$Cl$_2$ (75 ml) kept at room temperature. After 30', the mixture was evaporated and purified by flash chromatography as above described, obtaining the title compound as a pure oil.

EXAMPLE 4
[N-[2-Aminoethyl](S)-2-(hydroxymethyl)pyrrolidine]-2-keto-4-hydroxy-1-pyrrolidinoacetamide (formula I; with X=OH; n=1; m=2)

The mixture of methyl (±)2-keto-4-hydroxy-1-pyrrolidinoacetate (1.3 g) and of [N-(2-aminoethyl)(S)-2-(hydroxymethyl)]pyrrolidine (5.8 g) was warmed to 100° C. in an oil bath. After 2 hours, the unreacted ester and amine were evaporated and the residue was purified by flash chromatography with the CHCl$_3$/CH$_3$OH/ET$_3$N 99/5/2 system obtaining, with a 55% yield, the title product as a pure oil.

for C$_{13}$H$_{23}$N$_3$O$_4$: calc. % C 54.71, H 8.12, N 14.72. found % C 54.73, H 8.25, N 14.87.

EXAMPLE 5

(a)
[N-(2-Cyanoethyl)(S)-2-(hydroxymethyl)]pyrrolidine (S)-prolinol (0.053 mol.) was added to a suspension of NaH (57% in mineral oil, 4.5 g, 0.107 mol.) in THF (150 ml).

When the H$_2$ evolution was over, the mixture was refluxed and after cooling to the room temperature, 0.053 moles of acrylonitrile were added.

The suspension was warmed in autoclave to 60° for 16 hours and then evaporated under vacuo. The residue was mainly [N-(2-cyanoethyl)(S)-2-(hydroxymethyl)-]pyrrolidine, as determined by chromatography.

(b)
[N-(3-aminopropyl)(S)-2-(hydroxymethyl)]pyrrolidine

The solution in THF of the crude product obtained in (a) was reduced with LiAlH$_4$ (2 g) refluxing the suspension for 1.5 h. The mixture was then reduced, added with water (1.8 ml) and 10% NaOH (3.6 ml), stirred and filtered. The evaporation of the filtrate under vacuo gave a residue from which the oily product may be isolated by chromatography on silica eluting with CHCl$_3$/CH$_3$OH/ET$_3$N 95/5/1, b.p. 180°-185°.

for C$_8$H$_{14}$N$_2$O: calc. % C 62.33, H 9.09, N 18.18. found % C 62.24, H 9.31, H 18.09.

(c)
[N-[3-Aminopropyl](S)-2-(hydroxymethyl)pyrrolidine]-2-keto-1-pyrrolidinoacetamide (formula I; with X=H; n=1; m=3)

The mixture of methyl 2-keto-1-pyrrolidinoacetate (1.2 g) and of [[N-(3-aminopropyl)(S)-2-(hydroxymethyl)]pyrrolidine] (6 g) was heated to 100° in an oil bath. After 2,5 hours the unreacted ester and amine were evaporated under vacuo and the residue was purified by flash chromatography with the CHCl$_3$/MeOH/ET$_3$N 95/5/2 system obtaining a pure product (oil).

$[\alpha]_D^{20} = -32°$ (c=0.9% in CHCl$_3$).

for C$_{14}$H$_{25}$N$_3$O$_3$: calc. % C 59.36, H 8.83, N 14.84. found % C 59.44, H 8.79, N 14.93.

The present invention refers also to all the industrially applicable aspects connected with the use of compounds I as nootropic agents, particularly for the therapy of mental syndromes due to cerebral insufficiency and to troubles of the mental performance in the elderly patient.

An essential aspect of the invention is therefore provided by pharmaceutical compositions containing a compound I alone or combined with a pharmaceutical vehicle, in form of tablets, capsules, powders, granulates for oral solutions or suspensions, syrups.

The active ingredients may be alone in capsules. Otherwise they may be formulated using the usual pharmaceutical vehicle such as lactose or talc, granulating agent such as magnesium stearate and stearic acid, suspending agent such as methylcellulose and/or surfactants such as polyoxyethylenestearate; preservative agents such as ethyl p-hydroxybenzoate, flavouring agents, etc.

The pharmaceutical compositions of the present invention are preferably formulated in unit dosage form containing from 100 to 1.000 mg of the compound I in admixture with a pharmaceutical vehicle. Said unit doses may be administered once to three times a day.

I claim:

1. A pyrrolidin-2-one compound of formula I

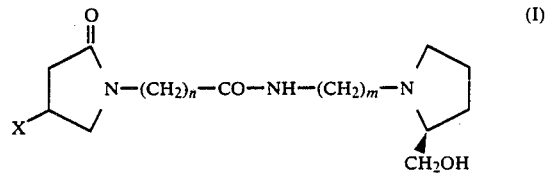

wherein X is hydrogen or an OR group, wherein R has one of the following meanings: hydrogen, saturated or unsaturated C$_1$-C$_6$ alkyl, cycloalkyl, aralkyl or phenyl; n represents zero or 1 and m represents 2 or 3.

2. A compound according to claim 1, wherein X=H, n=1 and m=2.

3. A compound according to claim 1, wherein X=OH, n=1, m=2.

4. A compound according to claim 1, wherein X=H, n=1 and m=3.

5. A pharmaceutical composition having nootropic activity, for use in the therapy of mental syndromes due to cerebral insufficiency and to troubles of mental performance of the elderly patient, comprising as the principal active ingredient a compound according to claim 1 in admixture with a pharmaceutically acceptable carrier.

* * * * *